United States Patent [19]

Hashimoto et al.

[11] 4,099,954

[45] Jul. 11, 1978

[54] AMIDE PHOSPHOROTHIOLATE HERBICIDES

[75] Inventors: Shunichi Hashimoto, Takarazuka; Kunio Mukai, Nishinomiya, both of Japan

[73] Assignee: Sumitomo Chemical Company, Limited, Japan

[21] Appl. No.: 713,595

[22] Filed: Aug. 11, 1976

[30] Foreign Application Priority Data

Aug. 28, 1975 [JP] Japan .................................. 50-104630
Mar. 31, 1976 [JP] Japan .................................. 51-36541

[51] Int. Cl.² .......................... A01N 9/36; C07F 9/65; C07F 9/60; C07F 9/18
[52] U.S. Cl. .................................. 71/87; 260/239 B; 260/283 P; 260/293.73; 260/293.85; 260/326.11 R; 260/326.5 A; 260/943; 544/157
[58] Field of Search .......... 260/239 B, 293.73, 293.85, 260/326.5 A; 71/87

[56] References Cited

U.S. PATENT DOCUMENTS

| | | | |
|---|---|---|---|
| 3,449,109 | 6/1969 | Richter | 71/87 |
| 3,752,869 | 8/1973 | Kiehs et al. | 260/943 |
| 3,776,984 | 12/1973 | Ratts | 260/943 |
| 3,833,600 | 9/1974 | Toepfl | 260/293.85 |
| 3,849,102 | 11/1974 | Bucha et al. | 71/76 |
| 3,955,957 | 5/1976 | Sturm et al. | 71/76 |
| 3,997,526 | 12/1976 | Satomi et al. | 260/239 B |
| 4,015,974 | 4/1977 | Satomi et al. | 71/87 |

FOREIGN PATENT DOCUMENTS 710,340   5/1965   Canada.

OTHER PUBLICATIONS

Bliznyuk et al., Chemical Abstracts 74, 142,055y (1971).

*Primary Examiner*—Donald G. Daus
*Assistant Examiner*—Diana G. Rivers
*Attorney, Agent, or Firm*—Wenderoth, Lind & Ponack

[57] ABSTRACT

The present invention relates to new herbicidal phosphorothioate (phosphorodithioate) derivatives and to preparation thereof.

5 Claims, No Drawings

AMIDE PHOSPHOROTHIOLATE HERBICIDES

The present invention provides a compound of the general formula (I):

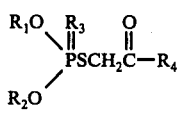

wherein $R_1$ and $R_2$ are each of the formula

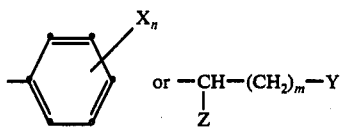

(in which X each is a lower alkyl group (preferably methyl) or halogen atom (preferably chlorine or bromine); Y is a halogen atom (preferably chlorine or bromine); Z is a hydrogen atom or methyl group; m is an integer of from 1 to 2; n is an integer of from 0 to 2); $R_3$ is an oxygen or sulfur atom; $R_4$ is a group of the formula

(but in such case $R_1$ and $R_2$ are each a group of the formula

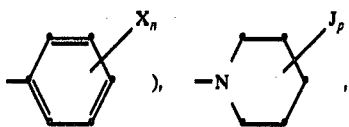

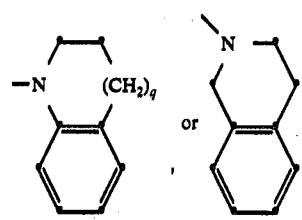

(in which A and B are each a lower alkyl (preferably $C_1 - C_4$ alkyl), lower alkenyl (preferably propenyl), lower alkynyl (preferably propynyl), benzyl, phenyl, or nitro or lower alkyl (preferably methyl) substituted phenyl group; J is a lower alkyl group (preferably $C_1 - C_2$ alkyl); p is an integer of 0 to 2; q is an integer of 0 to 1), pyrrolidino, hexamethyleneimino, morpholino or dimethylmorpholino group.

The invention also provides a method of making a compound of the invention (i.e. of the general formula I) which comprises reacting preferably in a solvent, e.g. water, an alcohol or a ketone or a mixture thereof, preferably at a temperature of from 20° C. to 100° C. and preferably for from one to several hours, a thiophosphate (dithiophosphate) of the general formula (II):

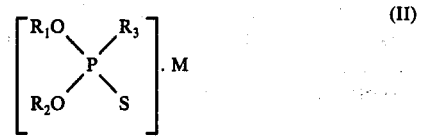

(in which $R_1$, $R_2$ and $R_3$ are each as defined above, and M is an alkali metal atom or an ammonium radical) with a halogenated compound of the general formula (III):

wherein $R_4$ is the same as defined above, and Hal is a halogen atom.

The invention also includes herbicidal composition including effective amounts of the compounds of the invention in combination with inert carrier. This composition can take the form of granules, dusts, wettable powders, emulsifiable concentrates or fine granules and can include one or more fertilizers, fungicides, insecticides, nematocides and/or herbicides.

The compounds of the present invention displays a strong herbicidal activity not only when used in both a preemergence treatment and a foliage treatment of weeds, but also on various kinds of weed including grassy weeds such as barnyard glass (*Echninochloa crusgalli*), large crabgrass (*Digitaria sanguinalis*) goose grass (*Eleusine indica*), water foxtail (*Alopecurus aequalis*) and annual bluegrass (*Poa annua*), broad-leaved weeds such as redroot pigweed (*Amaranthus retroflexus*), common purslane (*Portulaca oleracea*), smart weed sp. (*Poligonum sp.*), common lambsquarter (*Chenopodium album*), and weeds in paddy fields such as false pimpernel (*Linderna pyxidaria*), monochoria (*Monochoria viaginalis presl.*) and toothcut (*Rotala indica Koehue*); sedge weeds such as nutsedge sp. (*Cyperus diffforuds*) and slender spikerush (*Eleocharis acicularis*).

One of the most important properties of herbicides is that they can display a herbicidal activity on various kinds of weeds because, if they can control most kinds of weed but not a few other kinds of weeds, the remaining weeds will often grow and do harm to crops.

Therefore, the compounds of the present invention which can display a strong herbicidal activity on more kinds of weeds, can be said most suitable for a herbicide.

As prior art relating to the present invention there may be mentioned U.S. Pat. No. 3,385,689 and Swiss Pat. No. 496,398 wherein there are disclosed, for example, compounds of the formula:

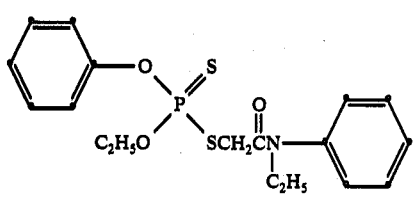

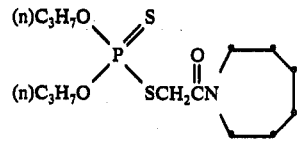

and which have herbicidal properties.

We have investigated the herbicidal activity of various derivatives of these phosphorothiolate compounds and have found that the compounds of the following structure:

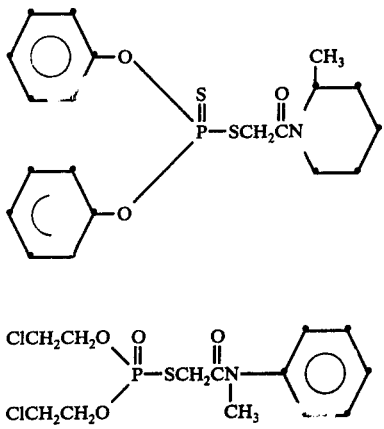

have excellent herbicidal efficacy. It has been surprising to find that the compounds of the formula (I) are excellent herbicides. Especially when a pre-emergence or pre-plant incorporation application is made, they shown remarkably good effect in killing weeds and yet they do not appear to have any phytotoxicity to cultivated plants.

The method of the present invention can preferably be carried out by condensing a salt of dithiophosphate (thiophosphate) of the formula (II) with halogenated compound of the formula (III) in the presence of solvents such as water, alcohols, ketones and if possible solvents which can dissolve the both starting materials completely therein. The reaction temperatures and reaction times vary depending upon the kinds of solvent and starting material, and in general the reaction can satisfactorily proceed at 20° to 100° C. for one to several hours. On completion of the reaction, the aimed products can readily be obtained in a very high purity by conventional treatments, however, if necessary, can further be purified by column-chromatography.

Some examples of the starting materials, i.e. dithiophosphate (thiophosphate) salts and halogenated compounds, which are used in the practice of the present invention will be shown as follows.

First, Examples of dithiophosphate (thiophosphate) salt are as follows, which are only illustrative but not limitative thereto:

sodium O,O-diphenyldithiophosphate,
sodium O,O-diphenylthiophosphate,
sodium O,O-di(4-methylphenyl)dithiophosphate,
sodium O,O-di(4-methylphenyl)thiophosphate,
sodium O,O-di(4-chlorophenyl)dithiophosphate,
sodium O,O-di(4-chlorophenyl)thiophosphate,
sodium O,O-di(2-methylphenyl)dithiophosphate,
sodium O,O-di(2-methylphenyl)thiophosphate,
sodium O,O-di(3-methylphenyl)dithiophosphate,
sodium O,O-di(3-methylphenyl)thiophosphate,
sodium O,O-di(4-chloro-2-methylphenyl)dithiophosphate,
sodium O,O-di(2,4-dichlorophenyl)dithiophosphate,
sodium O,O-di(4-bromophenyl)dithiophosphate,
sodium O,O-di(3,4-dimethylphenyl)dithiophosphate,
sodium O,O-di(3,5-dimethylphenyl)dithiophosphate,
sodium O,O-di(4-ethylphenyl)dithiophosphate,
sodium O,O-di(4-tert.-butylphenyl)dithiophosphate,
sodium O,O-di(4-chloro-3-methylphenyl)dithiophosphate,
potassium O,O-diphenyldithiophosphate,
ammonium O,O-diphenylthiophosphate,
sodium O,O-di-2-chloroethyldithiophosphate,
potassium O,O-di-2-chloroethyldithiophosphate,
sodium O,O-di-3-chloropropyl dithiophosphate,
potassium O,O-di-3-chloropropyldithiophosphate,
sodium O,O-di-1-methyl-2-chloroethyldithiophosphate,
potassium O,O-di-1-methyl-2-chloroethyldithiophosphate,
sodium O,O-di-2-bromoethyldithiophosphate,
potassium O,O-di-2-bromoethyldithiophosphate,
sodium O,O-di-2-chloroethylthiophosphate,
ammonium O,O-di-2-chloroethylthiophosphate,
sodium O,O-di-3-chloropropylthiophosphate,
ammonium O,O-di-3-chloropropylthiophosphate, and
ammonium O,O-di-1-methyl-2-chloroethylthiophosphate.

Examples of halogenated compound are as follows, which are only illustrative but not limitative thereto.

N-(α-chloroacetyl)-pyrrolidine,
N-(α-chloroacetyl)-piperidine,
N-(α-chloroacetyl)-2-methyl-piperidine,
N-(α-chloroacetyl)-3-methylpiperidine,
N-(α-chloroacetyl)-4-methylpiperidine,
N-(α-chloroacetyl)-2-ethylpiperidine,
N-(α-chloroacetyl)-hexamethyleneimine,
N-(α-chloroacetyl)-morpholine,
N-(α-chloroacetyl)-2,6-dimethyl morpholine,
1-(α-chloroacetyl)-1,2,3,4-tetrahydroquinoline,
N-(α-chloroacetyl)-2,6-dimethylpiperidine,
2-(α-chloroacetyl)-1,2,3,4-tetrahydroisoquinoline,
1-(α-chloroacetyl)-2,3-dihydroindole,
N-(α-bromoacetyl)-2-methylpiperidine,
N-(α-bromoacetyl)-piperidine,
N,N-diethyl-α-chloroacetamide,
N,N-dipropyl-α-chloroacetamide,
N,N-diallyl-α-chloroacetamide,
N,N-dibutyl-α-chloroacetamide,
N-methyl-N-phenyl-α-chloroacetamide,
N-ethyl-N-phenyl-α-chloroacetamide,
N-propargyl-N-phenyl-α-chloroacetamide,
N-propyl-N-phenyl-α-chloroacetamide,
N-(α-chloroacetyl)-2-methylpiperidine,
N-(α-chloroacetyl)-3-methylpiperidine,
N-(α-chloroacetyl)-4-methylpiperidine,
N-(α-chloroacetyl)-2-ethylpiperidine,
N-(α-chloroacetyl)-2-propylpiperidine,
N-methyl-N-2-methylphenyl-α-chloroacetamide,
N-methyl-N-benzyl-α-chloroacetamide,
N-(α-chloroacetyl)-piperidine,
N-(α-chloroacetyl)-pyrrolidine,
N-(α-chloroacetyl)-morpholine,
N-(α-chloroacetyl)-hexamethyleneimine,
1-(α-chloroacetyl)-1,2,3,4-tetrahydroquinoline,
N-(α-chloroacetyl)-2,3-dihydroindole,
N-(α-bromoacetyl)-2-methylpiperidine,
N-methyl-N-3-methylphenyl-α-chloroacetamide, and
N-methyl-N-4-nitrophenyl-α-chloroacetamide.

Next, some representative examples of the organic phosphoric acid ester of the present invention will concretely be shown as follows:
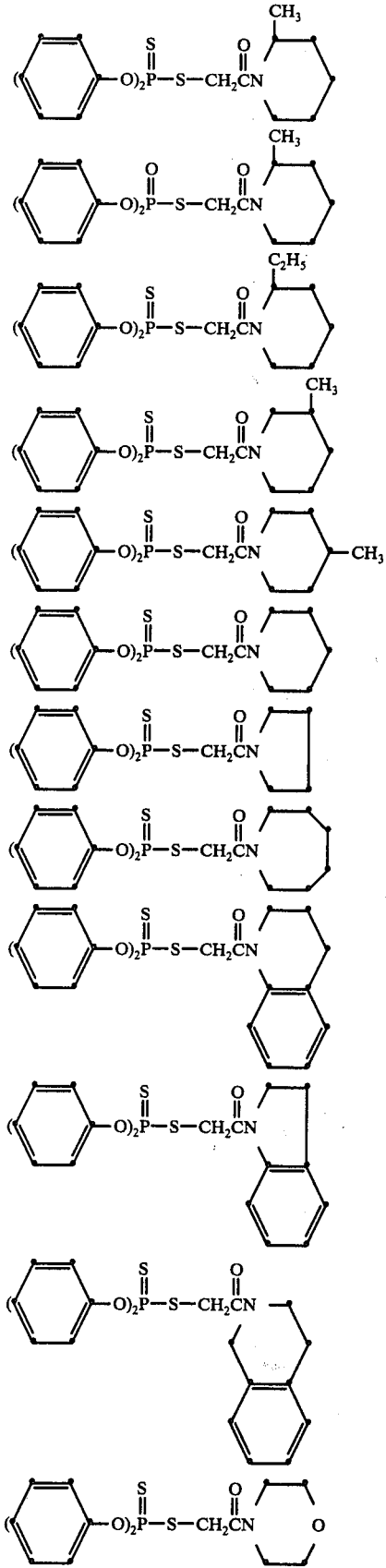
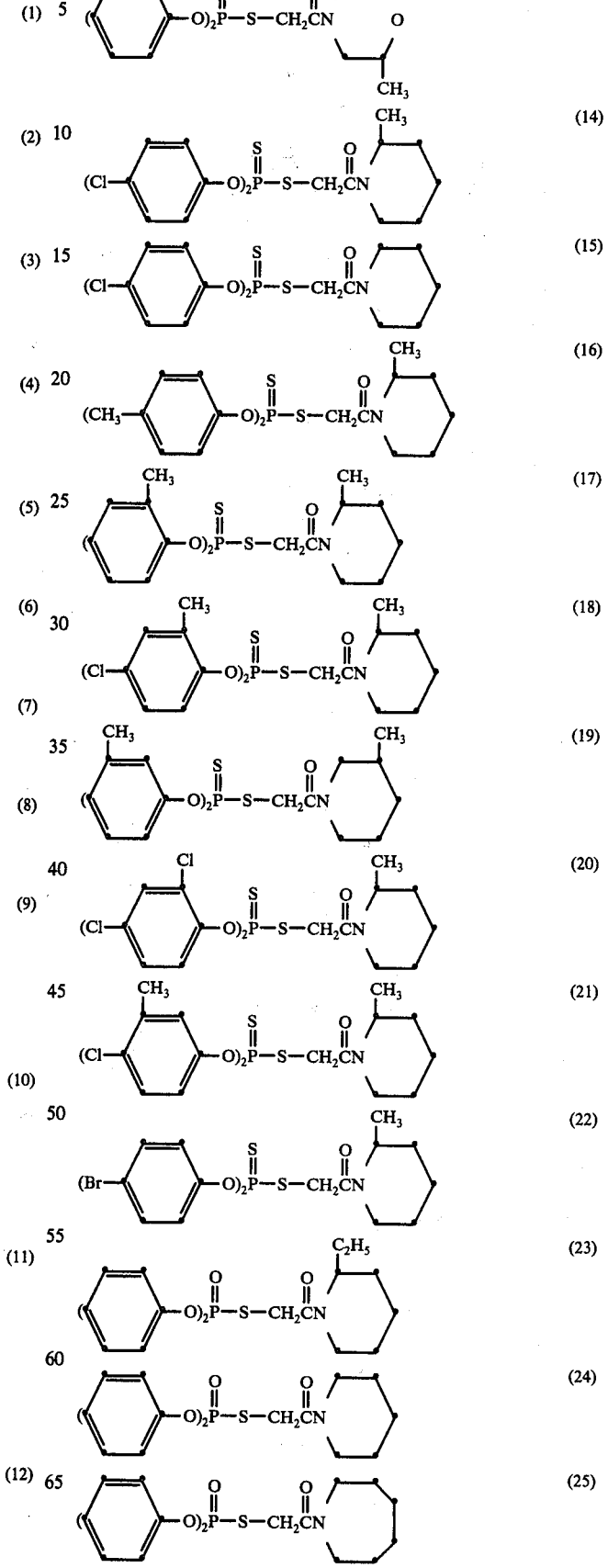

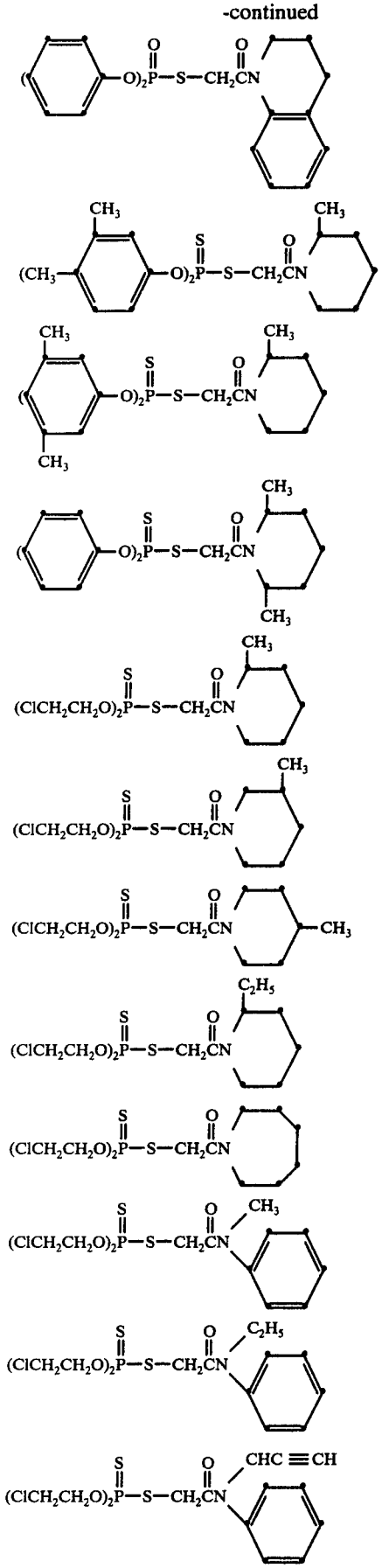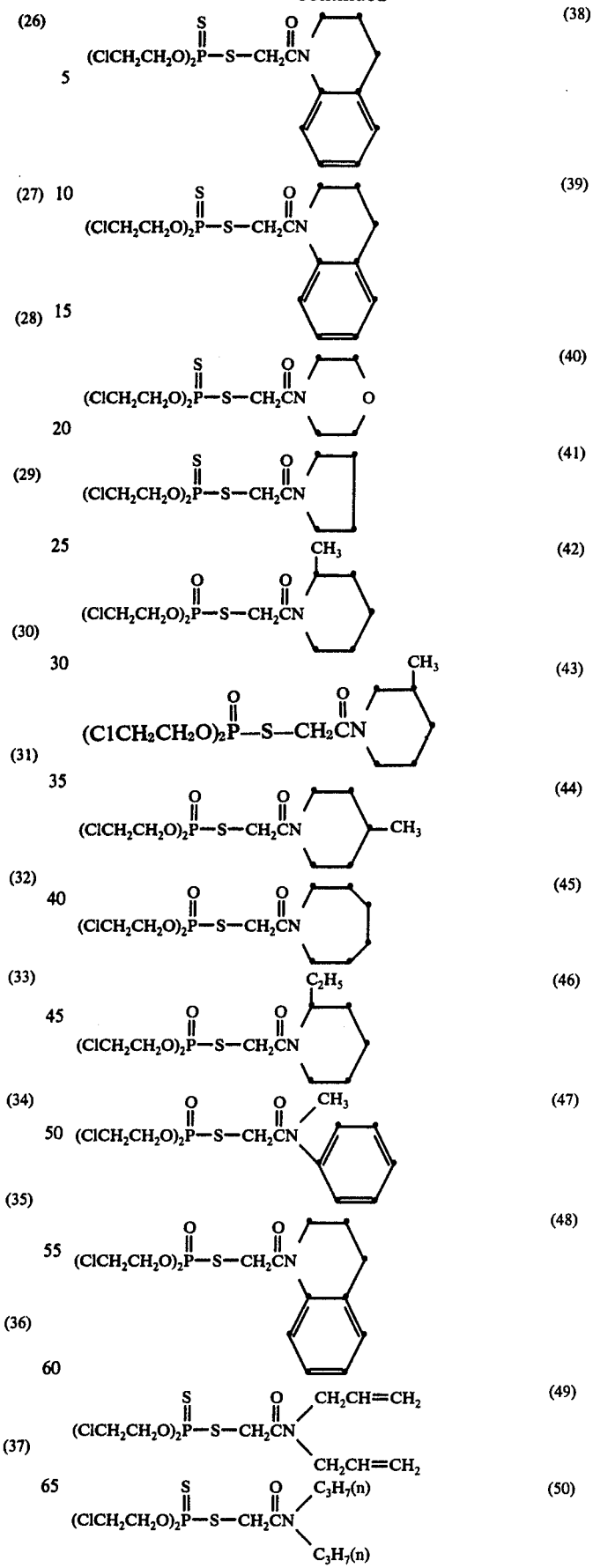

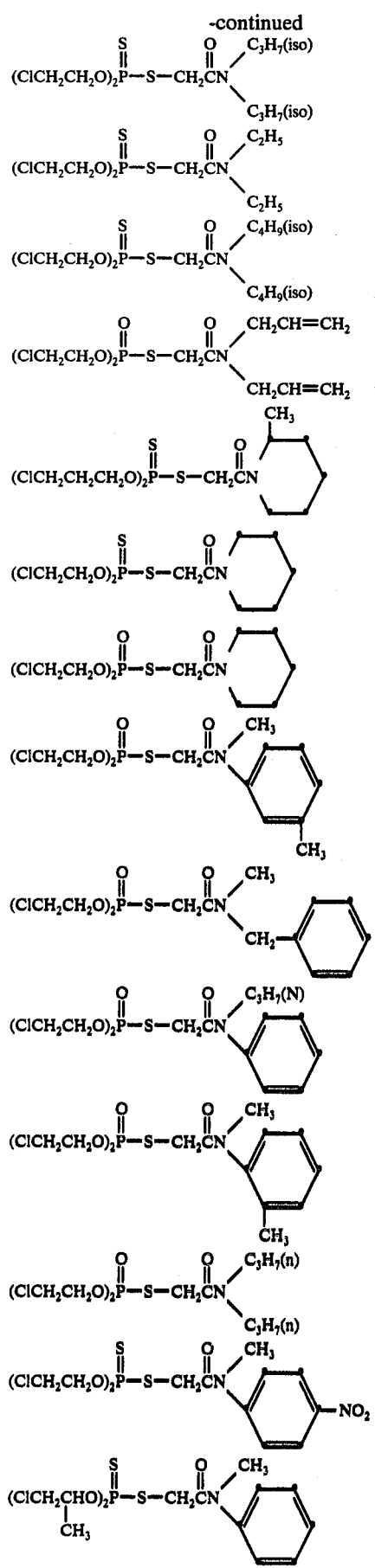
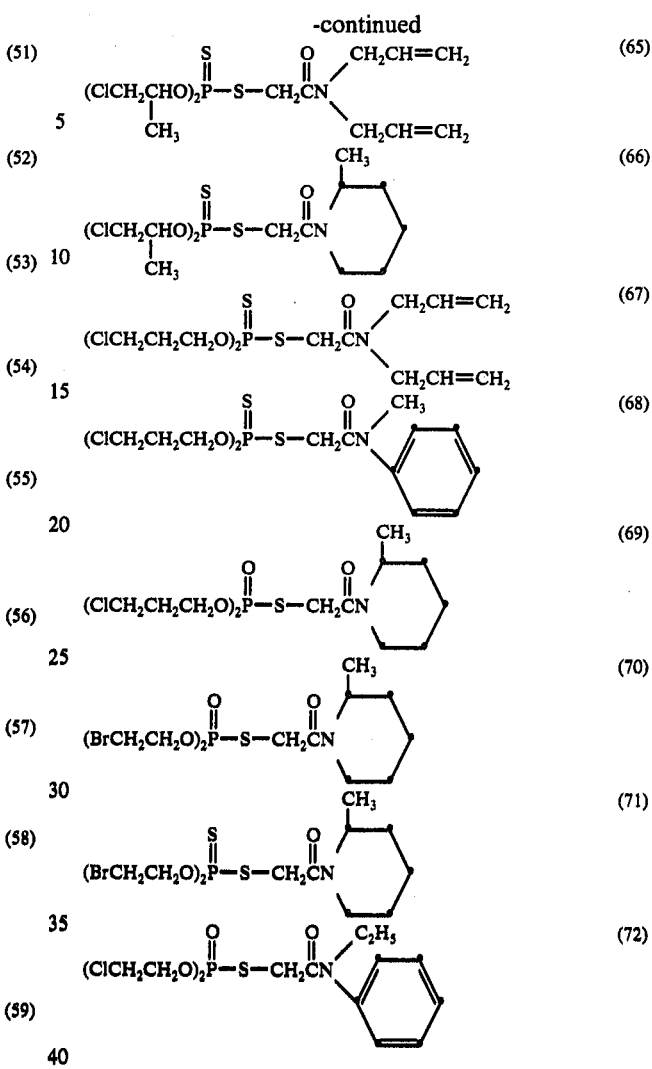

The compounds of the present invention, as described above, display a strong herbicidal activity on various kinds of weed, however one of the most noticeable features thereof is their herbicidal acitvity on more kinds of weed in addition to their strong herbicidal activity.

Moreover, the compounds of the present invention have other excellent properties as a herbicide, for example, a long persistency, an activity on both a pre-emergence treatment and a foliage treatment of weeds, and a selectivity to many crops such as rice plant, radish, soy bean, sugar best, cotton, pea, tomato, lettuce, wheat and corn. The present compounds are also useful as a herbicide for, needless to say, paddy rice fields, and cereals, vegetables, orchards, turfs, pasture lands, woods and forests and non-crop lands.

The present compounds, in actual application thereof, may be used as such or may be used in any preparation form of dusts, granules, fine granules, wettable powders and emulsifiable concentrates. In formulating those preparations, there are used solid carriers including talc, bentonite, clay, kaolin, diatomaceous earth, vermiculite and calcium hydroxide; and liquid carriers including benzene, alcohols, acetone, xylene, methylnaphthalene, dioxane and cyclohexanone.

In actual application, the present compounds may be enhanced in effectiveness by using them in condition with surfactants such as spreaders for agriculture. It is also possible to use the present compounds in combination with agricultural chemicals such as fungicides, microbial insecticide, pyrethroide type insecticides, other insecticides and other herbicides, or with fertilizers.

The composition of the present invention will be illustrated with reference to the following preparative examples.

PREPARATION 1

25 parts of the compound (1), 5 parts of a surfactant of polyoxyethylene acetylallylester type and 70 parts of talc were thoroughly mixed together by pulverizing to obtain a wettable powder.

PREPARATION 2

30 parts of the compound (2), 20 parts of a surfactant of polyethylene glycolester type and 50 parts of cyclohexanone were thoroughly mixed together to obtain an emulsifiable concentrate.

PREPARATION 3

5 parts of the compound (15), 40 parts of bentonite, 50 parts of clay and 5 parts of sodium lignosulfonate were thoroughly mixed together by pulverizing, sufficiently, kneading with water, granulated and dried to obtain granules.

PREPARATION 4

3 parts of the compound (30) and 97 parts of clay were thoroughly mixed together by pulverizing to obtain dusts.

PREPARATION 5

5 parts of the compound (42), 4 parts of sodium lignosulfonate, 86 parts of clay and 5 parts of water were thorougly kneaded in a ribbon mixer and dried to obtain fine granules.

PREPARATION 6

25 parts of the compound (60), 5 parts of a surfactant of polyoxyethylene acetylallylelster type and 70 parts of talc were thoroughly mixed together by pulverizing to obtain a wettable powder.

The present invention will be illustrated in more detail with reference to the following test examples, in which the names of compound are represented by the numbers of the compound exemplified above.

TEST EXAMPLE 1

Pre-emergence application.

Seeds of barnyard grass (*Echinochloa crus-galli*) and large crabgrass (*Digitaria sanguinalis*) as representative of grassy weeds and those of radish, redroot pigweed (*Amaranthus retroflexus*), common purslane (*Portulaca oleracea*) and common lambsquarter (*Chenopodium albus*) as representative of broad-leaved weeds were individually sown in flower pots of about 10 cm. in diameter. After covering the seeds with soil, test compounds as shown in Table 1 were individually applied to the soil treatment. Thereafter, the plants were grown in a green house and 20 days after application, the herbicidal effects of the compound were observed, the results of which are as shown in Table 1.

Herbicidal effects were evaluated by the numerals ranging from 0 (not damaged) to 5 (completely killed). All the test compounds were used in the form of wettable powder and diluted with water before application.

Table 1

| Comp. No. | Amount applied (g/a) | Barn-yard grass | Large crab-grass | Rad-ish | Red-root pig-weed | Common purs-lane | Common lambs-quarter |
|---|---|---|---|---|---|---|---|
| (1) | 80 | 5 | 5 | 0 | 5 | 5 | 5 |
|     | 40 | 5 | 5 | 0 | 4 | 4 | 4 |
|     | 20 | 4 | 5 | 0 | 3 | 4 | 3 |
| (2) | 80 | 5 | 5 | 0 | 4 | 4 | 4 |
|     | 40 | 5 | 5 | 0 | 4 | 4 | 3 |
|     | 20 | 5 | 5 | 0 | 3 | 3 | 3 |
| (3) | 80 | 4 | 4 | 0 | 4 | 3 | 3 |
| (4) | 160 | 5 | 5 | 0 | 4 | 4 | 4 |
|     | 80 | 5 | 5 | 0 | 3 | 3 | 3 |
| (5) | 160 | 5 | 5 | 0 | 4 | 4 | 3 |
|     | 80 | 5 | 5 | 0 | 3 | 2 | 2 |
| (6) | 60 | 5 | 5 | 0 | 4 | 4 | 4 |
|     | 40 | 5 | 5 | 0 | 3 | 3 | 3 |
| (7) | 80 | 5 | 5 | 0 | 3 | 4 | 4 |
| (8) | 160 | 5 | 5 | 0 | 5 | 5 | 5 |
|     | 80 | 5 | 5 | 0 | 4 | 4 | 4 |
|     | 40 | 5 | 5 | 0 | 4 | 4 | 4 |
| (14) | 160 | 4 | 4 | 0 | 4 | 3 | 4 |
| (15) | 160 | 4 | 4 | 0 | 4 | 4 | 4 |
| (30) | 40 | 5 | 5 | 0 | 5 | 5 | 5 |
|     | 20 | 5 | 5 | 0 | 5 | 5 | 5 |
|     | 10 | 5 | 5 | 0 | 5 | 5 | 5 |
| (31) | 40 | 5 | 5 | 0 | 5 | 5 | 5 |
|     | 20 | 5 | 5 | 0 | 5 | 5 | 4 |
|     | 10 | 4 | 5 | 0 | 4 | 5 | 4 |
| (32) | 40 | 5 | 5 | 0 | 5 | 5 | 5 |
|     | 20 | 5 | 5 | 0 | 4 | 4 | 4 |
|     | 10 | 5 | 4 | 0 | 4 | 4 | 4 |
| (33) | 40 | 5 | 5 | 0 | 5 | 5 | 5 |
|     | 20 | 5 | 5 | 0 | 4 | 5 | 4 |
|     | 10 | 5 | 4 | 0 | 4 | 4 | 4 |
| (34) | 40 | 5 | 5 | 0 | 4 | 4 | 4 |
|     | 20 | 5 | 4 | 0 | 4 | 4 | 3 |
| (35) | 40 | 5 | 5 | 0 | 5 | 5 | 5 |
|     | 20 | 5 | 5 | 0 | 5 | 5 | 5 |
|     | 10 | 4 | 5 | 0 | 4 | 5 | 4 |
| (36) | 40 | 5 | 5 | 0 | 5 | 5 | 5 |
|     | 20 | 5 | 5 | 0 | 5 | 5 | 5 |
|     | 10 | 4 | 5 | 0 | 5 | 5 | 4 |
| (37) | 40 | 5 | 5 | 0 | 5 | 5 | 5 |
|     | 20 | 5 | 5 | 0 | 5 | 5 | 5 |
|     | 10 | 4 | 5 | 0 | 4 | 4 | 4 |
| (38) | 40 | 5 | 5 | 0 | 5 | 5 | 5 |
|     | 20 | 5 | 5 | 0 | 5 | 5 | 5 |
|     | 10 | 5 | 5 | 0 | 4 | 5 | 4 |
| (39) | 40 | 5 | 5 | 0 | 5 | 5 | 5 |
|     | 20 | 5 | 5 | 0 | 5 | 5 | 5 |
|     | 10 | 4 | 5 | 0 | 4 | 4 | 4 |
| (40) | 40 | 5 | 5 | 0 | 5 | 5 | 5 |
|     | 20 | 5 | 4 | 0 | 4 | 4 | 4 |
| (41) | 40 | 5 | 4 | 0 | 4 | 4 | 4 |
| (42) | 40 | 5 | 5 | 0 | 5 | 5 | 5 |
|     | 20 | 5 | 5 | 0 | 5 | 5 | 5 |
|     | 10 | 5 | 5 | 0 | 5 | 5 | 5 |
| (43) | 40 | 5 | 5 | 0 | 5 | 5 | 5 |
|     | 20 | 5 | 5 | 0 | 5 | 5 | 5 |
|     | 10 | 5 | 5 | 0 | 5 | 5 | 5 |
| (44) | 40 | 5 | 5 | 0 | 5 | 5 | 5 |
|     | 20 | 5 | 5 | 0 | 5 | 5 | 5 |
|     | 10 | 5 | 5 | 0 | 5 | 5 | 5 |
| (45) | 40 | 5 | 5 | 0 | 5 | 5 | 5 |
|     | 20 | 5 | 5 | 0 | 5 | 5 | 5 |
|     | 10 | 5 | 5 | 0 | 5 | 5 | 5 |
| (46) | 40 | 5 | 5 | 0 | 5 | 5 | 5 |
|     | 20 | 5 | 5 | 0 | 4 | 5 | 4 |
|     | 10 | 5 | 5 | 0 | 4 | 4 | 3 |
| (47) | 40 | 5 | 5 | 0 | 5 | 5 | 5 |
|     | 20 | 5 | 5 | 0 | 5 | 5 | 5 |
|     | 10 | 5 | 5 | 0 | 5 | 5 | 5 |
| (48) | 40 | 5 | 5 | 0 | 5 | 5 | 5 |
|     | 20 | 5 | 5 | 0 | 5 | 5 | 5 |
|     | 10 | 5 | 5 | 0 | 5 | 5 | 5 |
| (49) | 40 | 5 | 5 | 0 | 5 | 5 | 5 |
|     | 20 | 5 | 5 | 0 | 5 | 5 | 5 |
|     | 10 | 5 | 5 | 0 | 5 | 5 | 5 |
| (50) | 40 | 5 | 5 | 0 | 5 | 5 | 5 |
|     | 20 | 5 | 5 | 0 | 5 | 5 | 5 |
|     | 10 | 5 | 5 | 0 | 5 | 5 | 5 |
| (51) | 40 | 5 | 5 | 0 | 5 | 5 | 5 |
|     | 20 | 5 | 5 | 0 | 5 | 5 | 5 |
|     | 10 | 5 | 5 | 0 | 5 | 5 | 5 |
| (52) | 40 | 5 | 5 | 0 | 4 | 5 | 4 |
|     | 20 | 5 | 5 | 0 | 4 | 5 | 4 |
|     | 10 | 5 | 5 | 0 | 4 | 4 | 3 |
| (53) | 40 | 5 | 5 | 0 | 5 | 5 | 5 |
|     | 20 | 4 | 5 | 0 | 4 | 4 | 4 |
|     | 10 | 4 | 4 | 0 | 4 | 4 | 3 |
| (54) | 40 | 5 | 5 | 0 | 5 | 5 | 5 |
|     | 20 | 5 | 5 | 0 | 5 | 5 | 5 |

Table 1-continued

| Comp. No. | Amount applied (g/a) | Barn-yard grass | Large crab-grass | Rad-ish | Red-root pig-weed | Common purs-lane | Common lambs-quarter |
|---|---|---|---|---|---|---|---|
| | 10 | 5 | 5 | 0 | 5 | 5 | 5 |
| (55) | 40 | 5 | 5 | 0 | 4 | 4 | 4 |
| (56) | 40 | 5 | 5 | 0 | 4 | 4 | 3 |
| (57) | 40 | 5 | 5 | 0 | 5 | 5 | 5 |
| | 20 | 5 | 5 | 0 | 4 | 5 | 4 |
| (58) | 40 | 5 | 5 | 0 | 5 | 5 | 5 |
| | 20 | 5 | 5 | 0 | 4 | 4 | 4 |
| (59) | 40 | 5 | 5 | 0 | 5 | 5 | 5 |
| | 20 | 5 | 5 | 0 | 4 | 4 | 4 |
| (60) | 80 | 5 | 5 | 0 | 4 | 4 | 3 |
| | 40 | 5 | 5 | 0 | 5 | 5 | 5 |
| (61) | 20 | 5 | 5 | 0 | 5 | 5 | 5 |
| | 10 | 5 | 5 | 0 | 5 | 5 | 5 |
| (62) | 40 | 5 | 5 | 0 | 5 | 5 | 5 |
| | 20 | 4 | 4 | 0 | 4 | 5 | 4 |
| (63) | 160 | 4 | 5 | 0 | 4 | 4 | 4 |
| (64) | 160 | 5 | 5 | 0 | 5 | 5 | 5 |
| | 80 | 4 | 5 | 0 | 4 | 5 | 4 |
| (65) | 40 | 5 | 4 | 0 | 4 | 5 | 4 |
| | 20 | 4 | 4 | 0 | 4 | 4 | 3 |
| (66) | 80 | 5 | 5 | 0 | 5 | 4 | 4 |
| | 40 | 4 | 5 | 0 | 4 | 4 | 4 |
| (67) | 40 | 5 | 5 | 0 | 4 | 4 | 4 |
| | 20 | 4 | 5 | 0 | 4 | 4 | 4 |
| (68) | 40 | 5 | 5 | 0 | 5 | 5 | 4 |
| | 20 | 5 | 5 | 0 | 4 | 4 | 4 |
| (69) | 40 | 5 | 5 | 0 | 5 | 5 | 4 |
| | 20 | 5 | 5 | 0 | 4 | 4 | 4 |
| (70) | 40 | 5 | 5 | 0 | 4 | 5 | 4 |
| | 20 | 5 | 5 | 0 | 3 | 4 | 4 |
| (71) | 40 | 5 | 5 | 0 | 4 | 4 | 4 |
| (72) | 20 | 5 | 5 | 0 | 5 | 5 | 5 |
| | 10 | 5 | 5 | 0 | 5 | 5 | 5 |
| | 20 | 5 | 5 | 0 | 5 | 5 | 5 |
| V | 10 | 4 | 3 | 0 | 2 | 3 | 2 |
| | 5 | 2 | 1 | 0 | 0 | 1 | 0 |
| PCP [1] | 100 | 3 | 4 | 4 | 4 | 4 | 4 |
| | 50 | 2 | 2 | 1 | 2 | 2 | 2 |

Note: [1] Chemical structure

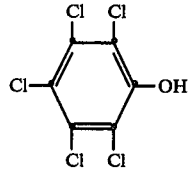

TEST EXAMPLE 2

Water application

Wagner posts of 14 cm. in diameter, which had been packed with 1.5 kg. of paddy field soil, were placed in paddy fields. To the pots were transplanted rice seedlings at the 3-leave stage. Further, seeds of barnyard grass (*Echinochloa crus-galli*) were sown in the pots and the required amounts of test compounds were applied to the soil water logged condition. 25 days after application, the herbicidal activity and phytotoxicity were investigated on the above-mentioned plants which had been transplanted and sown and on broad-leaved weeds, e.g. monochoria (*Monochoria viaginalis Presl.*), false pimpernel (*Linderna pyxidaria*) and toothcup (*Rotala indica Koehue*), which had been spontaneously germinated. The test compounds were used in the form of wettable powder. The results obtained are as shown in Table 2. The herbicidal effects and the phytotoxicity were evaluated as follows by the numerals ranging from 0 to 5.

Table 2

| Compound No. | Amount applied (g/a) | Barnyard grass | Broad-leaved weeds | Phytotoxicity on rice |
|---|---|---|---|---|
| (1) | 40 | 5 | 5 | 0 |
| | 20 | 5 | 5 | 0 |
| | 10 | 5 | 5 | 0 |
| (2) | 80 | 5 | 5 | 1 |
| | 40 | 5 | 5 | 0 |
| | 20 | 5 | 5 | 0 |
| (3) | 40 | 5 | 5 | 0 |
| | 20 | 5 | 4 | 0 |
| | 10 | 5 | 4 | 0 |
| (4) | 40 | 5 | 5 | 0 |
| | 20 | 5 | 5 | 0 |
| | 10 | 4 | 4 | 0 |
| (5) | 80 | 5 | 5 | 0 |
| | 40 | 5 | 5 | 0 |
| | 20 | 5 | 5 | 0 |
| (6) | 40 | 5 | 5 | 0 |
| | 20 | 5 | 5 | 0 |
| | 10 | 5 | 4 | 0 |
| (7) | 40 | 5 | 5 | 0 |
| | 20 | 5 | 5 | 0 |
| | 10 | 5 | 4 | 0 |
| (8) | 40 | 5 | 5 | 0 |
| | 20 | 5 | 5 | 0 |
| | 10 | 5 | 5 | 0 |
| (14) | 80 | 5 | 5 | 0 |
| | 40 | 5 | 5 | 0 |
| | 20 | 5 | 5 | 0 |
| (15) | 80 | 5 | 5 | 0 |
| | 40 | 5 | 5 | 0 |
| | 20 | 5 | 4 | 0 |
| (16) | 80 | 5 | 5 | 0 |
| | 40 | 5 | 5 | 0 |
| | 20 | 4 | 4 | 0 |
| (30) | 40 | 5 | 5 | 0 |
| | 20 | 5 | 5 | 0 |
| | 10 | 5 | 5 | 0 |
| (31) | 40 | 5 | 5 | 0 |
| | 20 | 5 | 5 | 0 |
| | 10 | 5 | 5 | 0 |
| (32) | 40 | 5 | 5 | 0 |
| | 20 | 5 | 5 | 0 |
| | 10 | 5 | 5 | 0 |
| (33) | 40 | 5 | 5 | 1 |
| | 20 | 5 | 5 | 0 |
| | 10 | 5 | 5 | 0 |
| (34) | 40 | 5 | 5 | 0 |
| | 20 | 5 | 5 | 0 |
| | 10 | 5 | 5 | 0 |
| (35) | 40 | 5 | 5 | 0 |
| | 20 | 5 | 5 | 0 |
| | 10 | 5 | 5 | 0 |
| (36) | 40 | 5 | 5 | 0 |
| | 20 | 5 | 5 | 0 |
| | 10 | 5 | 5 | 0 |
| (37) | 40 | 5 | 5 | 0 |
| | 20 | 5 | 5 | 0 |
| | 10 | 5 | 5 | 0 |
| (38) | 40 | 5 | 5 | 0 |
| | 20 | 5 | 5 | 0 |
| | 10 | 5 | 5 | 0 |
| (39) | 40 | 5 | 5 | 0 |
| | 20 | 5 | 5 | 0 |
| | 10 | 5 | 5 | 0 |
| (40) | 40 | 5 | 5 | 0 |
| | 20 | 5 | 4 | 0 |
| (41) | 40 | 5 | 5 | 0 |
| | 20 | 5 | 5 | 0 |

Table 2-continued

Herbicidal effects

| Compound No. | Amount applied (g/a) | Barnyard grass | Broad-leaved weeds | Phytotoxicity on rice |
|---|---|---|---|---|
| (42) | 20 | 5 | 5 | 1 |
|  | 10 | 5 | 5 | 0 |
| (43) | 40 | 5 | 5 | 0 |
|  | 20 | 5 | 5 | 0 |
|  | 10 | 5 | 5 | 0 |
| (44) | 40 | 5 | 5 | 0 |
|  | 20 | 5 | 5 | 0 |
|  | 10 | 5 | 5 | 0 |
| (45) | 40 | 5 | 5 | 0 |
|  | 20 | 5 | 5 | 0 |
|  | 10 | 4 | 5 | 0 |
| (46) | 40 | 5 | 5 | 0 |
|  | 20 | 5 | 4 | 0 |
| (47) | 40 | 5 | 5 | 1 |
|  | 20 | 5 | 5 | 0 |
|  | 10 | 5 | 5 | 0 |
| (48) | 40 | 5 | 5 | 0 |
|  | 20 | 5 | 5 | 0 |
|  | 10 | 5 | 5 | 0 |
| (49) | 40 | 5 | 5 | 0 |
|  | 20 | 5 | 5 | 0 |
|  | 10 | 5 | 5 | 0 |
| (50) | 40 | 5 | 5 | 0 |
|  | 20 | 5 | 5 | 0 |
|  | 10 | 5 | 5 | 0 |
| (51) | 40 | 5 | 5 | 0 |
|  | 20 | 5 | 5 | 0 |
|  | 10 | 5 | 5 | 0 |
| (52) | 40 | 5 | 5 | 0 |
|  | 20 | 5 | 5 | 0 |
|  | 10 | 5 | 5 | 0 |
| (53) | 40 | 5 | 5 | 0 |
|  | 20 | 5 | 5 | 0 |
|  | 10 | 5 | 5 | 0 |
| (54) | 40 | 5 | 5 | 0 |
|  | 20 | 5 | 5 | 0 |
|  | 10 | 5 | 5 | 0 |
| (55) | 40 | 5 | 5 | 0 |
|  | 20 | 5 | 5 | 0 |
|  | 10 | 5 | 5 | 0 |
| (56) | 40 | 5 | 5 | 0 |
|  | 20 | 5 | 5 | 0 |
| (57) | 40 | 5 | 5 | 1 |
|  | 20 | 5 | 5 | 0 |
|  | 10 | 5 | 5 | 0 |
| (58) | 40 | 5 | 5 | 0 |
|  | 20 | 5 | 5 | 0 |
|  | 10 | 5 | 5 | 0 |
| (59) | 40 | 5 | 5 | 0 |
|  | 20 | 5 | 5 | 0 |
|  | 10 | 5 | 5 | 0 |
| (60) | 40 | 5 | 5 | 0 |
|  | 20 | 5 | 5 | 0 |
|  | 10 | 5 | 4 | 0 |
| (61) | 80 | 5 | 4 | 0 |
|  | 40 | 4 | 4 | 0 |
| (62) | 80 | 5 | 4 | 0 |
|  | 40 | 5 | 4 | 0 |
| (63) | 80 | 3 | 3 | 0 |
|  | 40 | 3 | 3 | 0 |
| (64) | 40 | 5 | 5 | 0 |
|  | 20 | 5 | 5 | 0 |
|  | 10 | 5 | 4 | 0 |
| (65) | 40 | 5 | 5 | 0 |
|  | 20 | 5 | 5 | 0 |
|  | 10 | 5 | 5 | 0 |
| (66) | 40 | 5 | 5 | 0 |
|  | 20 | 5 | 5 | 0 |
|  | 10 | 5 | 5 | 0 |
| (67) | 40 | 5 | 5 | 0 |
|  | 20 | 5 | 5 | 0 |
|  | 10 | 5 | 5 | 0 |
| (68) | 40 | 5 | 5 | 0 |
|  | 20 | 5 | 5 | 0 |
|  | 10 | 5 | 5 | 0 |
| (69) | 40 | 5 | 5 | 0 |
|  | 20 | 5 | 5 | 0 |
|  | 10 | 5 | 5 | 0 |
| (70) | 40 | 5 | 5 | 0 |
|  | 20 | 5 | 5 | 0 |
|  | 10 | 5 | 5 | 0 |
| (71) | 40 | 5 | 5 | 0 |
|  | 20 | 5 | 5 | 0 |
|  | 10 | 5 | 5 | 0 |
| (72) | 40 | 5 | 5 | 0 |
|  | 20 | 5 | 5 | 0 |
|  | 10 | 5 | 5 | 0 |
| IV | 40 | 5 | 3 | 0 |
|  | 20 | 4 | 2 | 0 |
|  | 10 | 2 | 1 | 0 |
| Nip [1] (control) | 40 | 5 | 5 | 4 |
|  | 20 | 5 | 5 | 2 |

Note: 1) Chemical structure

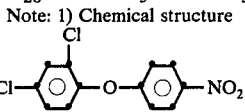

Effect on plants
0 no effect
1 very slightly affected
2 slightly affected
3 moderately affected
4 considerably affected
5 completely killed The synthetic method according to the present invention will be illustrated with reference to the following examples which are only illustrative but not limitative thereto.

EXAMPLE 1

(Compound No. 1)

13.4 Grams of sodium 0,0-diphenyldithiophosphate were dissolved in 100 ml. of acetone, and the solution was added with 7.0 grams of N-(α-chloroacetyl)-2-methyl piperidine and refluxed for one hour while stirring. After removing acetone under reduced pressure, the residue was dissolved in toluene, and the solution was washed with an aqueous 3% sodium hydroxide solution and then with water. The solvent was then removed by a vacuum distillation and 16.2 grams of N-[α-(O,O-diphenylthiophosphorylthio)acetyl]-2-methyl piperidine were obtained as a pale yellow oil residue. Refractive index $n_D^{19.0}$ 1.5990

| Elementary analysis: | Calculated as $C_{20}H_{24}NO_3PS_2$ (%) | Found (%) |
|---|---|---|
| C | 56.99 | 56.63 |
| H | 5.74 | 5.70 |
| N | 3.32 | 3.51 |
| P | 7.35 | 7.41 |

Employing the same procedure as stated in Example 1, compounds (2) to (29) were prepared.

EXAMPLE 2

(Compound No. 30)

31.0 Grams of sodium O,O-di-2-chloroethyldithiophosphate were dissolved in 100 ml. of acetone and 17.5 grams of N-α-chloroacetyl-2-methyl piperidine were added thereto. Thus obtained solution was refluxed for 2 hours while stirring. Thereafter, acetone was removed under reduced pressure, the residue was added with toluene, and the toluene solution was washed successively with 5% sodium carbonate solution and with water. By removing toluene under reduced pressure, 36.0 grams of yellow oily product were obtained. The crude oil was subjected to a silica gel column chromatography and 32.0 grams of N-(α-O,O-di-2-chloroethylthiophosphorylthioacetyl)-2-methyl piperidine (refractive index $n_D^{20.5}$ 1.5500) were obtained as a colorless clear oil.

| Elementary analysis: | Calculated as $C_{12}H_{22}Cl_2NO_3PS_2$ (%) | Found (%) |
|---|---|---|
| C | 36.55 | 36.38 |
| H | 5.62 | 5.65 |
| N | 3.55 | 3.81 |
| P | 7.85 | 7.76 |

The intermediate of the dithiophosphate may be easily obtained by neutralizing a dithiophosphoric acid prepared by reacting the corresponding halo-alcohol with phosphorous dipentasulfite in the presence or absence of a solvent as toluene and the like.

The intermediate of the thiophosphate may be easily obtained by reacting the corresponding alcohol with phosphorous trichloride in a solvent such as carbon tetrachloride and the like to obtain diester phosphite and saturating the latter, in the presence of sulfur atom, with an ammonia gas.

Using the same procedure, other compounds (31) to (72) were prepared.

| Compound No. | Physical const. | Elementary analysis |  |  |
|---|---|---|---|---|
|  |  |  | Cald. (%) | Found (%) |
| (2) | $n_D^{23.0}$ 1.5680 | C | 59.25 | 59.22 |
|  |  | H | 5.97 | 5.91 |
|  |  | N | 3.46 | 3.48 |
|  |  | P | 7.64 | 7.48 |
| (3) | $n_D^{23.0}$ 1.5897 | C | 57.91 | 57.60 |
|  |  | H | 6.02 | 6.00 |
|  |  | N | 3.22 | 3.24 |
|  |  | P | 7.11 | 7.15 |
| (4) | $n_D^{22.0}$ 1.5925 | C | 56.99 | 57.07 |
|  |  | H | 5.74 | 5.68 |
|  |  | N | 3.32 | 3.71 |
|  |  | P | 7.35 | 7.30 |
| (5) | $n_D^{20.0}$ 1.5963 | C | 56.99 | 56.64 |
|  |  | H | 5.74 | 5.60 |
|  |  | N | 3.32 | 3.0 |
|  |  | P | 7.35 | 7.21 |

-continued

| Compound No. | Physical const. | Elementary analysis |  |  |
|---|---|---|---|---|
|  |  |  | Cald. (%) | Found (%) |
| (6) | $n_D^{20.5}$ 1.6060 | C | 56.00 | 56.12 |
|  |  | H | 5.44 | 5.25 |
|  |  | N | 3.44 | 3.68 |
|  |  | P | 7.60 | 7.80 |
| (7) | $n_D^{20.5}$ 1.6122 | C | 54.95 | 54.97 |
|  |  | H | 5.12 | 5.07 |
|  |  | N | 3.56 | 3.63 |
|  |  | P | 7.87 | 8.00 |
| (8) | $n_D^{20.0}$ 1.6010 | C | 56.99 | 56.67 |
|  |  | H | 5.74 | 5.67 |
|  |  | N | 3.32 | 3.21 |
|  |  | P | 7.35 | 7.10 |
| (9) | $n_D^{23.5}$ 1.6319 | C | 60.64 | 60.91 |
|  |  | H | 4.87 | 4.89 |
|  |  | N | 3.08 | 3.20 |
|  |  | P | 6.80 | 6.51 |
| (10) | m.p. 77 – 80° C. | C | 59.85 | 59.98 |
|  |  | H | 4.57 | 4.61 |
|  |  | N | 3.17 | 3.00 |
|  |  | P | 7.01 | 7.15 |
| (11) | $n_D^{22.5}$ 1.6255 | C | 60.64 | 60.60 |
|  |  | H | 4.87 | 4.94 |
|  |  | N | 3.08 | 3.15 |
|  |  | P | 6.80 | 6.52 |
| (12) | $n_D^{22.5}$ 1.6032 | C | 52.80 | 53.10 |
|  |  | H | 4.92 | 4.97 |
|  |  | N | 3.42 | 3.29 |
|  |  | P | 7.56 | 7.28 |
| (13) | $n_D^{20.0}$ 1.5801 | C | 54.90 | 55.11 |
|  |  | H | 5.53 | 5.63 |
|  |  | N | 3.20 | 3.27 |
|  |  | P | 7.08 | 6.75 |
| (14) | $n_D^{20.0}$ 1.5921 | C | 48.98 | 49.03 |
|  |  | H | 4.52 | 4.68 |
|  |  | Cl | 14.46 | 14.12 |
|  |  | N | 2.86 | 2.67 |
|  |  | P | 6.31 | 5.90 |
| (15) | $n_D^{20.0}$ 1.6052 | C | 47.90 | 47.64 |
|  |  | H | 4.23 | 4.47 |
|  |  | Cl | 14.88 | 14.97 |
|  |  | N | 2.94 | 2.84 |
|  |  | P | 6.50 | 6.70 |
| (16) | $n_D^{20.0}$ 1.5884 | C | 58.78 | 58.48 |
|  |  | H | 6.28 | 6.41 |
|  |  | N | 3.12 | 2.75 |
|  |  | P | 6.89 | 6.70 |
| (17) | $n_D^{20.0}$ 1.5893 | C | 58.78 | 58.98 |
|  |  | H | 6.28 | 6.31 |
|  |  | N | 3.12 | 3.10 |
|  |  | P | 6.89 | 6.56 |
| (18) | $n_D^{21.0}$ 1.5972 | C | 50.97 | 51.10 |
|  |  | H | 5.06 | 5.00 |
|  |  | Cl | 13.68 | 13.48 |
|  |  | N | 2.70 | 2.60 |
|  |  | P | 5.97 | 5/70 |
| (19) | $n_D^{20.0}$ 1.5886 | C | 58.78 | 58.89 |
|  |  | H | 6.28 | 6.25 |
|  |  | N | 3.12 | 3.10 |
|  |  | P | 6.89 | 6.76 |
| (20) | $n_D^{20.5}$ 1.5873 | C | 42.95 | 43.21 |
|  |  | H | 3.60 | 3.55 |
|  |  | Cl | 25.35 | 25.04 |
|  |  | N | 2.50 | 2.48 |
|  |  | P | 5.54 | 5.51 |
| (21) | $n_D^{22.0}$ 1.5965 | C | 50.97 | 51.18 |
|  |  | H | 5.06 | 5.15 |
|  |  | Cl | 13.68 | 13.79 |
|  |  | N | 2.70 | 2.68 |
|  |  | P | 5.97 | 5.95 |
| (22) | $n_D^{23.0}$ 1.6089 | C | 41.47 | 41.61 |
|  |  | H | 3.83 | 3.80 |
|  |  | Br | 27.59 | 27.36 |
|  |  | N | 2.42 | 2.60 |
|  |  | P | 5.35 | 5.31 |

| Compound No. | Physical const. | Elementary analysis | | |
|---|---|---|---|---|
| | | | Cald. (%) | Found (%) |
| (23) | $n_D^{21.0}$ 1.5590 | C<br>H<br>N<br>P | 60.13<br>6.25<br>3.34<br>7.38 | 60.22<br>6.23<br>3.30<br>7.15 |
| (24) | $n_D^{21.0}$ 1.5760 | C<br>H<br>N<br>P | 58.30<br>5.67<br>3.58<br>7.91 | 58.52<br>5.61<br>3.60<br>7.90 |
| (25) | $n_D^{22.0}$ 1.5710 | C<br>H<br>N<br>P | 59.25<br>5.97<br>3.46<br>7.64 | 59.44<br>6.05<br>3.41<br>7.57 |
| (26) | $n_D^{21.0}$ 1.6019 | C<br>H<br>N<br>P | 62.86<br>5.05<br>3.19<br>7.05 | 63.05<br>5.13<br>3.24<br>6.83 |
| (27) | $n_D^{22.0}$ 1.5784 | C<br>H<br>N<br>P | 60.35<br>6.75<br>2.93<br>6.48 | 60.51<br>6.74<br>2.89<br>6.30 |
| (28) | $n_D^{22.0}$ 1.5791 | C<br>H<br>N<br>P | 60.35<br>6.75<br>2.93<br>6.48 | 60.55<br>6.83<br>2.90<br>6.23 |
| (29) | $n_D^{20.0}$ 1.5890 | C<br>H<br>N<br>P | 57.91<br>6.02<br>3.22<br>7.11 | 58.25<br>6.00<br>3.18<br>7.05 |
| (30) | $n_D^{20.0}$ 1.5500 | C<br>H<br>Cl<br>N<br>P | 36.55<br>5.62<br>17.98<br>3.55<br>7.85 | 36.62<br>5.63<br>17.78<br>3.62<br>7.92 |
| (31) | $n_D^{23.5}$ 1.5501 | C<br>H<br>Cl<br>N<br>P | 36.55<br>5.62<br>17.98<br>3.55<br>7.85 | 36.61<br>5.60<br>17.75<br>3.64<br>7.92 |
| (32) | $n_D^{23.0}$ 1.5485 | C<br>H<br>Cl<br>N<br>P | 36.55<br>5.62<br>17.98<br>3.55<br>7.85 | 36.60<br>5.63<br>17.83<br>3.61<br>7.94 |
| (33) | $n_D^{18.0}$ 1.5178 | C<br>H<br>Cl<br>N<br>P | 38.24<br>5.92<br>17.36<br>3.43<br>7.58 | 38.51<br>5.88<br>17.27<br>3.40<br>7.47 |
| (34) | $n_D^{28.5}$ 1.5536 | C<br>H<br>Cl<br>N<br>P | 36.55<br>5.62<br>17.98<br>3.55<br>7.85 | 36.29<br>5.51<br>17.82<br>3.37<br>7.81 |
| (35) | $n_D^{19.0}$ 1.5745 | C<br>H<br>Cl<br>N<br>P | 38.81<br>4.51<br>17.63<br>3.48<br>7.70 | 39.19<br>4.57<br>17.43<br>3.65<br>7.62 |
| (36) | $n_D^{21.0}$ 1.5690 | C<br>H<br>Cl<br>N<br>P | 40.39<br>4.84<br>17.03<br>3.37<br>7.44 | 40.55<br>4.91<br>17.26<br>3.33<br>7.36 |
| (37) | $n_D^{20.5}$ 1.5643 | C<br>H<br>Cl<br>N<br>P | 42.26<br>4.25<br>16.63<br>3.29<br>7.26 | 42.05<br>4.22<br>16.75<br>3.30<br>7.08 |
| (38) | $n_D^{24.0}$ 1.5973 | C<br>H<br>Cl<br>N<br>P | 42.06<br>4.71<br>16.55<br>3.27<br>7.23 | 42.42<br>4.81<br>16.78<br>3.20<br>7.05 |
| (39) | $n_D^{21.0}$ 1.6021 | C<br>H<br>Cl<br>N<br>P | 40.59<br>4.38<br>17.11<br>3.38<br>7.47 | 40.82<br>4.41<br>17.39<br>3.35<br>7.30 |
| (40) | $n_D^{29.0}$ 1.5577 | C<br>H<br>Cl<br>N<br>P | 31.42<br>4.75<br>18.55<br>3.66<br>8.10 | 31.41<br>4.70<br>18.47<br>3.75<br>8.19 |
| (41) | $n_D^{20.0}$ 1.5648 | C<br>H<br>Cl<br>N<br>P | 32.79<br>4.95<br>19.36<br>3.83<br>8.46 | 32.92<br>4.91<br>19.58<br>3.85<br>8.27 |
| (42) | $n_D^{20.5}$ 1.5198 | C<br>H<br>Cl<br>N<br>P | 38.10<br>5.86<br>18.75<br>3.70<br>8.19 | 38.18<br>5.55<br>18.56<br>3.78<br>8.40 |
| (43) | $n_D^{27.5}$ 1.5179 | C<br>H<br>Cl<br>N<br>P | 38.10<br>5.86<br>18.75<br>3.70<br>8.19 | 38.22<br>5.81<br>18.56<br>3.89<br>8.20 |
| (44) | $n_D^{27.5}$ 1.5145 | C<br>H<br>Cl<br>N<br>P | 38.10<br>5.86<br>18.75<br>3.70<br>8.19 | 38.34<br>6.15<br>18.96<br>3.74<br>8.37 |
| (45) | $n_D^{27.5}$ 1.5210 | C<br>H<br>Cl<br>N<br>P | 38.10<br>5.86<br>18.75<br>3.70<br>8.19 | 38.26<br>6.02<br>18.56<br>3.67<br>8.32 |
| (46) | $n_D^{27.5}$ 1.5362 | C<br>H<br>Cl<br>N<br>P | 39.80<br>6.17<br>18.08<br>3.57<br>7.89 | 40.16<br>6.36<br>18.59<br>3.57<br>7.90 |
| (47) | $n_D^{18.0}$ 1.5482 | C<br>H<br>Cl<br>N<br>P | 40.43<br>4.70<br>18.36<br>3.63<br>8.02 | 40.44<br>4.65<br>18.27<br>3.90<br>8.10 |
| (48) | $n_D^{25.5}$ 1.5670 | C<br>H<br>Cl<br>N<br>P | 43.70<br>4.89<br>17.20<br>3.40<br>7.51 | 43.41<br>5.20<br>17.49<br>3.22<br>7.80 |
| (49) | $n_D^{21.0}$ 1.5489 | C<br>H<br>Cl<br>N<br>P | 36.74<br>5.14<br>18.07<br>3.57<br>7.89 | 36.54<br>5.05<br>18.25<br>3.51<br>8.16 |
| (50) | $n_D^{21.0}$ 1.5271 | C<br>H<br>Cl<br>N<br>P | 36.37<br>6.10<br>17.89<br>3.53<br>7.81 | 36.56<br>6.03<br>17.76<br>3.48<br>7.92 |
| (51) | $n_D^{24.0}$ 1.5149 | C<br>H<br>Cl<br>N<br>P | 36.37<br>6.10<br>17.89<br>3.53<br>7.81 | 36.58<br>6.08<br>17.91<br>3.48<br>7.66 |
| (52) | $n_D^{21.0}$ 1.5320 | C<br>H<br>Cl<br>N<br>P | 32.61<br>5.47<br>19.25<br>3.80<br>8.41 | 32.99<br>5.47<br>19.02<br>3.51<br>8.80 |
| (53) | $n_D^{23.0}$ 1.5216 | C<br>H<br>Cl<br>N<br>P | 39.62<br>6.65<br>16.71<br>3.30<br>7.30 | 39.95<br>6.77<br>16.96<br>3.25<br>7.50 |
| | | C | 38.31 | 38.24 |

-continued

| Compound No. | Physical const. | Elementary analysis | Cald. (%) | Found (%) |
|---|---|---|---|---|
| (54) | $n_D^{26.5}$ 1.5164 | H | 5.36 | 5.33 |
|  |  | Cl | 18.85 | 18.59 |
|  |  | N | 3.72 | 3.70 |
|  |  | P | 8.23 | 8.28 |
| (55) | $n_D^{21.0}$ 1.5457 | C | 39.81 | 39.78 |
|  |  | H | 6.21 | 6.32 |
|  |  | Cl | 16.79 | 16.55 |
|  |  | N | 3.32 | 3.40 |
|  |  | P | 7.33 | 7.40 |
| (56) | $n_D^{28.5}$ 1.5557 | C | 34.74 | 34.54 |
|  |  | H | 5.30 | 5.21 |
|  |  | Cl | 18.65 | 18.46 |
|  |  | N | 3.68 | 3.47 |
|  |  | P | 8.14 | 8.10 |
| (57) | $n_D^{18.0}$ 1.5230 | C | 36.27 | 36.10 |
|  |  | H | 5.53 | 5.59 |
|  |  | Cl | 19.47 | 19.24 |
|  |  | N | 3.85 | 3.75 |
|  |  | P | 8.50 | 8.70 |
| (58) | $n_D^{22.0}$ 1.5428 | C | 42.01 | 42.03 |
|  |  | H | 5.04 | 5.30 |
|  |  | Cl | 17.72 | 17.52 |
|  |  | N | 3.50 | 3.40 |
|  |  | P | 7.74 | 7.80 |
| (59) | $n_D^{22.0}$ 1.5471 | C | 42.01 | 42.26 |
|  |  | H | 5.04 | 5.08 |
|  |  | Cl | 17.72 | 17.39 |
|  |  | N | 3.50 | 3.60 |
|  |  | P | 7.74 | 7.81 |
| (60) | $n_D^{24.5}$ 1.5341 | C | 43.49 | 43.25 |
|  |  | H | 5.35 | 5.61 |
|  |  | Cl | 17.12 | 17.25 |
|  |  | N | 3.38 | 3.26 |
|  |  | P | 7.48 | 7.72 |
| (61) | $n_D^{24.5}$ 1.5382 | C | 42.01 | 42.40 |
|  |  | H | 5.04 | 5.41 |
|  |  | Cl | 17.72 | 17.59 |
|  |  | N | 3.50 | 3.42 |
|  |  | P | 7.74 | 8.00 |
| (62) | $n_D^{27.5}$ 1.4961 | C | 37.90 | 38.00 |
|  |  | H | 6.36 | 6.62 |
|  |  | Cl | 18.65 | 18.48 |
|  |  | N | 3.68 | 3.51 |
|  |  | P | 8.14 | 8.50 |
| (63) | $n_D^{19.0}$ 1.6016 | C | 34.91 | 35.21 |
|  |  | H | 3.83 | 3.54 |
|  |  | Cl | 15.85 | 15.77 |
|  |  | N | 6.26 | 6.45 |
|  |  | P | 6.92 | 7.00 |
| (64) | $n_D^{21.0}$ 1.5632 | C | 41.86 | 41.72 |
|  |  | H | 5.15 | 5.29 |
|  |  | Cl | 16.48 | 16.36 |
|  |  | N | 3.26 | 3.34 |
|  |  | P | 7.20 | 7.30 |
| (65) | $n_D^{20.0}$ 1.5380 | C | 40.00 | 39.65 |
|  |  | H | 5.75 | 5.54 |
|  |  | Cl | 16.87 | 16.62 |
|  |  | N | 3.33 | 3.31 |
|  |  | P | 7.37 | 7.50 |
| (66) | $n_D^{23.0}$ 1.5413 | C | 39.81 | 39.86 |
|  |  | H | 6.21 | 5.93 |
|  |  | Cl | 16.79 | 16.97 |
|  |  | N | 3.32 | 3.28 |
|  |  | P | 7.33 | 7.50 |
| (67) | $n_D^{20.5}$ 1.5419 | C | 40.00 | 40.02 |
|  |  | H | 5.75 | 5.66 |
|  |  | Cl | 16.87 | 16.64 |
|  |  | N | 3.33 | 3.43 |
|  |  | P | 7.37 | 7.60 |
| (68) | $n_D^{20.5}$ 1.5683 | C | 41.86 | 42.10 |
|  |  | H | 5.15 | 5.00 |
|  |  | Cl | 16.48 | 16.26 |
|  |  | N | 3.26 | 3.43 |
|  |  | P | 7.20 | 7.30 |
|  |  | C | 41.39 | 41.62 |
|  |  | H | 6.45 | 6.57 |
| (69) | $n_D^{21.0}$ 1.5128 | Cl | 17.45 | 17.61 |
|  |  | N | 3.45 | 3.40 |
|  |  | P | 7.62 | 7.50 |
| (70) | $n_D^{22.0}$ 1.5402 | C | 30.85 | 31.08 |
|  |  | H | 4.75 | 4.83 |
|  |  | Br | 34.21 | 34.60 |
|  |  | N | 3.00 | 3.05 |
|  |  | P | 6.63 | 6.46 |
| (71) | $n_D^{21.0}$ 1.5709 | C | 29.83 | 30.14 |
|  |  | H | 4.59 | 4.72 |
|  |  | Br | 33.07 | 33.19 |
|  |  | N | 2.90 | 2.88 |
|  |  | P | 6.41 | 6.72 |
| (72) | $n_D^{27.5}$ 1.5362 | C | 42.01 | 42.35 |
|  |  | H | 5.04 | 5.31 |
|  |  | Cl | 17.72 | 17.92 |
|  |  | N | 3.50 | 3.70 |
|  |  | P | 7.74 | 7.13 |

What is claimed is:

1. A compound of the formula:

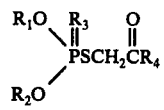

wherein $R_1$ and $R_2$ are each a group of the formula

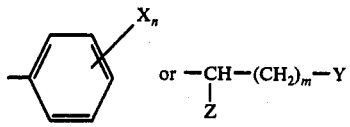

in which X is lower alkyl or halogen; Y is halogen; Z is hydrogen or methyl; m is an integer of 1 to 2; n is an integer of from 0 to 2; $R_3$ is oxygen or sulfur; $R_4$ is

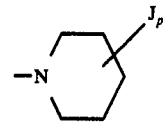

in which J is lower alkyl and p is an integer of from 0 to 2; pyrrolidino or hexamethyleneimino.

2. The compound according to claim 1, wherein $R_1$ and $R_2$ are each a group of the formula

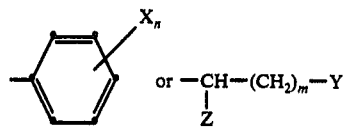

in which X is methyl, chlorine or bromine; Y is chlorine or bromine; Z is a hydrogen or methyl; m is an integer of from 1 to 2; n is an integer from 0 to 2; $R_3$ is oxygen or sulfur; $R_4$ is a group of the formula

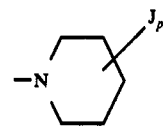

in which J is $C_1$ – $C_2$ alkyl and $p$ is an integer of from 0 to 2; pyrrolidino or hexamethylemeimino.

3. A compound of the formula;

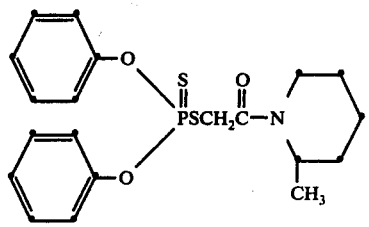

4. A herbicidal composition which comprises as an active ingredient an effective amount of the compound according to claim 1, and an inert carrier.

5. A method for controlling the undesired growth of grasses or weeds which comprises applying an effective amount of the compound according to claim 1 to the area where the control of the grasses or weeds is desired.

* * * * *